United States Patent [19]

Pfluger

[11] Patent Number: 4,542,216
[45] Date of Patent: Sep. 17, 1985

[54] PROCESS FOR PRODUCING FLUOROALKOXYAMINOPYRIMIDINES

[75] Inventor: Rudolf W. Pfluger, Münchenstein, Switzerland

[73] Assignee: Ciba Geigy Corporation, Ardsley, N.Y.

[21] Appl. No.: 593,218

[22] Filed: Mar. 27, 1984

[51] Int. Cl.$^4$ .......................................... C07D 239/02
[52] U.S. Cl. .................... 544/320; 544/319; 544/321
[58] Field of Search .................... 544/319, 320, 321

[56] References Cited

U.S. PATENT DOCUMENTS 4,480,101  10/1984  Meyer ................................ 544/320

FOREIGN PATENT DOCUMENTS 70802  1/1983  European Pat. Off. .
70804  1/1983  European Pat. Off. .
84020  7/1983  European Pat. Off. .
94790  11/1983  European Pat. Off. .

OTHER PUBLICATIONS

Pissiotas et al., Chem. Abst. 101:211162w (1984).
Meyer, Chem. Abst. 99:22486j, 98:215616q (1983).
Tamura et al., Chem. Abst. 83:2314t (1975).
Chem. Listy 52, 357 (1958), Jaroslav Stanek.

Primary Examiner—Donald G. Daus
Assistant Examiner—Cecilia Shen
Attorney, Agent, or Firm—Karl F. Jorda

[57] ABSTRACT

A novel process for producing fluoroalkoxyaminopyrimidines of the formula I

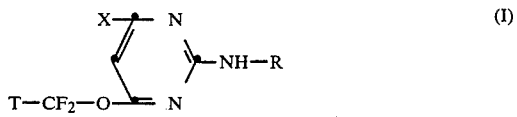

wherein R is hydrogen, $C_1$–$C_4$-alkyl, $C_1$–$C_4$-alkoxy or benzyl, X is halogen, $C_1$–$C_4$-alkyl, $C_1$–$C_4$-alkoxy, $C_1$–$C_4$-haloalkyl, $C_1$–$C_4$-haloalkoxy, $C_1$–$C_4$-alkylamino or di-$C_1$–$C_4$-alkylamino, and T is hydrogen, chlorofluoromethyl, bromofluoromethyl, difluoromethyl or 1,2,2,2-tetrafluoroethyl, characterized in that a thiopyrimidine of the formula II

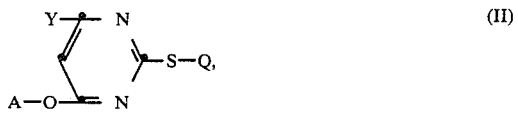

wherein Y has the meaning given for X under the formula I or is hydroxyl, A is hydrogen, sodium, potassium or an equivalent of calcium or magnesium, and Q is $C_1$–$C_4$-alkyl, phenyl or benzyl, is reacted with difluorochloromethane, difluorobromomethane, tetrafluoroethylene, perfluoropropylene, trifluorobromoethylene or trifluorochloroethylene in the presence of a base; the resulting compound of the formula III

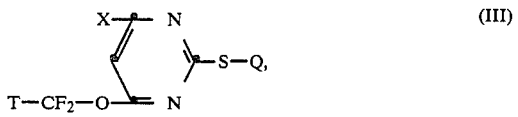

is converted by oxidation into a compound of the formula IV

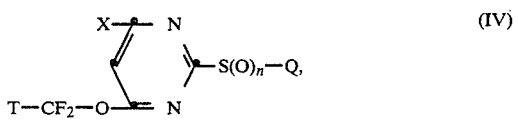

wherein n is the number one or two; and this compound is treated with an amine of the formula V

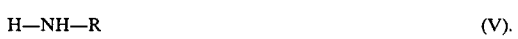

H—NH—R          (V).

31 Claims, No Drawings

PROCESS FOR PRODUCING FLUOROALKOXYAMINOPYRIMIDINES

The present invention relates to a novel process for producing fluoroalkoxyaminopyrimidines, and also to intermediates developed for the novel process.

The fluoroalkoxyaminopyrimidines obtainable by the novel process according to the invention are valuable intermediates for herbicidal and plant-growth-regulating active substances of the sulfonylurea class. Such active substances, together with their biological effects, are described for example in the European Patent Application Publications Nos. EP-A 70802, EP-A 84020 and EP-A 94790.

Fluoroalkoxyaminopyrimidines, which can be produced also by the novel process according to the present invention, are described in the European Patent Application Publication No. EP-A 70804, together with a process for producing them, as well as a synthesis process for converting them into the herbicidal and plant-growth-regulating sulfonylureas.

The process disclosed in EP-A 70804 for producing fluoroalkoxy- and fluoroalkylthioaminopyrimidines by reaction of corresponding aminopyrimidines with difluorochloromethane, difluorobromomethane and fluoroalkenes, in the presence of bases, yields the desired fluoroalkoxyaminopyrimidines in low to medium yields. The conversion in this process is not complete, with the result that regeneration of the starting material from the reaction solutions is necessary.

There is hence a need for a process for producing the intermediates, which process would render possible the synthesis of the desired compounds in high yields, and at the same time render unnecessary the uneconomical recovery of unreacted starting material.

It has now been established that, surprisingly, the novel process according to the present invention for producing the fluoroalkoxyaminopyrimidines largely meets the hitherto existing need for such a process.

With use of the process according to the invention, the fluoroalkoxyaminopyrimidines of the formula I

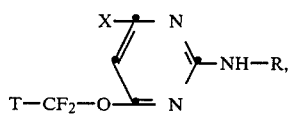

wherein R is hydrogen, $C_1$-$C_4$-alkyl, $C_1$-$C_4$-alkoxy or benzyl, X is halogen, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino or di-$C_1$-$C_4$-alkylamino, and T is hydrogen, chlorofluoromethyl, bromofluoromethyl, difluoromethyl or 1,2,2,2-tetrafluoroethyl, can be produced by reacting a thiopyrimidine of the formula II

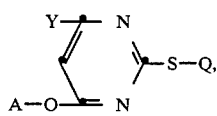

wherein Y has the meaning given for X under the formula I or is hydroxyl, Q is $C_1$-$C_4$-alkyl, phenyl or benzyl, and A is hydrogen, sodium, potassium or an equivalent of calcium or magnesium, with difluoromethane, difluorobromomethane, tetrafluoroethylene, perfluoropropylene, trifluorobromoethylene or trifluorochloroethylene in the presence of a base; converting the resulting compound of the formula III

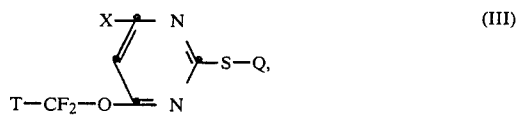

wherein T and X have the meanings defined under the formula I and Q the meanings defined under the formula II, by oxidation into a compound of the formula IV

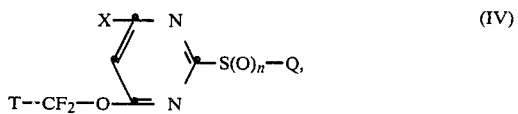

wherein T and X have the meanings defined under the formula I and Q the meanings defined under the formula II, and n is the number one or two; and treating this compound with an amine of the formula V

wherein R has the meaning given under the formula I.

In the definitions of the symbols under the formulae I, II, III, IV and V, the generic terms: alkyl, alkoxy and halogen, or collective terms, such as haloalkyl, haloalkoxy, alkylamino or dialkylamino, have for example the following meanings: alkyl is methyl, ethyl, n-propyl, i-propyl or the four isomeric butyl groups; alkoxy is methoxy, ethoxy, n-propyloxy, i-propyloxy or the four isomeric butyloxy groups; and halogen is fluorine, chlorine, bromine or iodine. Preferred halogen atoms are fluorine and chlorine. The haloalkyl, haloalkoxy, alkylamino and dialkylamino groups are composed analogously. Preferred radicals from these groups are: fluoromethyl, 2,2,2-trifluoroethoxy, difluoromethoxy, fluoromethoxy, trifluoromethyl, trifluoromethoxy, perfluoroethyl, 1,1,2,2-tetrafluoroethoxy, methylamino, ethylamino, dimethylamino or diethylamino. The alkyl chains in the stated radicals preferably each contain one or two carbon atoms.

The individual reaction steps of the process according to the invention are all advantageously performed in an inert solvent or inert solvent mixture. Also included are solvent combinations consisting of solvents which amongst each other do not form a homogeneous phase. Such mixtures are in general known as "liquid two-phase systems".

The first step of the process according to the invention is the fluoroalkylation of the free hydroxyl functions of the thiopyrimidine of the formula II. In place of the free hydroxyl compounds of the formula II, it is possible to use for this reaction step also sodium, potassium, magnesium or calcium salts thereof. This reaction step is performed essentially in a manner analogous to that of known etherification reactions. The reaction of the compound of the formula II surprisingly results in the intermediate product of the formula III being obtained in high yield. The use of an inert polar solvent or solvent mixture has proved to be of advantage in this reaction step. Suitable solvents are: ethers, such as diethyl ether, ethylene glycol dimethyl ether, diethylene glycol dimethyl ether, diisopropyl ether, dioxane or tetrahydrofuran; alcohols, such as methanol, ethanol, propanol or i-propanol; ketones, such as acetone, 2-butanone or cyclohexanone, or water, dimethylformamide, acetonitrile or dimethyl sulfoxide. Preferred solvents are: tetrahydrofuran, dioxane, methanol, ethanol, i-propanol, acetone, 2-butanone, water, dimethylformamide, acetonitrile or dimethyl sulfoxide. Suitable bases are in general inorganic bases from the series: hydrides, such as sodium hydride or calcium hydride; oxides, such as magnesium oxide, calcium oxide or sodium oxide; hydroxides, such as lithium hydroxide, sodium hydroxide or potassium hydroxide; or carbonates, such as sodium carbonate or potassium carbonate. With the use of gaseous or low-boiling fluoroalkylation agents, it is sometimes advisable to perform the reaction under an elevated pressure of between 1 bar and 100 bar, preferably between 1 bar and 20 bar. Suitable reaction vessels for carrying out the reaction under elevated pressure are autoclaves. The reaction temperatures are held, depending on the nature of the reactants of the formula II and of the fluoroalkylation agent, between 0° and 120° C., preferably between 20° and 100° C. In suitable cases, the base can be added in the form of an aqueous solution. Where no homogeneous phase is formed, but a two-phase mixture, it can be advantageous to add to the reaction mixture a phase-transfer catalyst, for example a customary quaternary ammonium salt or a crown ether.

When there are used starting products of the formula II which contain two hydroxyl functions or salt forms thereof (Y is hydroxyl), homogeneous reaction products are then obtained only if both hydroxyl groups are etherified with the use of corresponding amounts of the fluoroalkylating agent.

A preferred embodiment of the first stage of the process according to the invention comprises carrying out the reaction of the compound of the formula II to the compound of the formula III at a temperature of between 20° and 100° C., under a pressure of 1 bar to 20 bar, in the presence of a base from the series: sodium hydride, calcium hydride, sodium hydroxide, potassium hydroxide, sodium carbonate and potassium carbonate, and in a solvent from the group comprising: dioxane, tetrahydrofuran, methanol, ethanol, i-propanol, acetone, 2-butanone, water, dimethylformamide, acetonitrile and dimethyl sulfoxide, or in a mixture of these solvents.

The second step of the process according to the invention is the oxidation of the —S—Q group of the compound of the formula III into an —SO—Q or —SO$_2$—Q group to obtain a compound of the formula IV. Oxidising agents that can be used are customary reagents, such as organic peroxides, organic peroxy acids, hypochlorites, hydrogen peroxide, potassium permanganate, osmium tetroxide and ruthenium tetroxide. Preferred oxidising agents are: 3-chloroperoxybenzoic acid, peroxybenzoic acid, monoperoxyphthalic acid, peroxyacetic acid, peroxyformic acid, hydrogen peroxide, sodium hypochlorite or potassium permanganate.

The oxidation (III→IV) is advantageously performed in an inert solvent. Solvents suitable for the oxidation are for example: methylene chloride, chloroform, carbon tetrachloride, tetrachloroethane, trichloroethane, chlorobenzene, dichlorobenzene, trichlorobenzene, cyclopentane, cyclohexane, acetic acid, formic acid or water. It is of advantage also to carry out the reaction in mixtures of these solvents. In the case of two-phase, liquid solvent systems, the addition of a customary phase-transfer catalyst, for example a quaternary ammonium salt or a crown ether, may be advisable. A temperature of between −20° and +90° C., especially between −20° and +25° C., is preferably used for performing the oxidation step.

A preferred embodiment of the second step of the process according to the invention comprises performing the oxidation of a compound of the formula III to a compound of the formula IV at a temperature of between −20° and +25° C. in a solvent selected from the group: methylene chloride, chloroform, carbon tetrachloride, tetrachloroethane, trichloroethane, chlorobenzene, dichlorobenzene, trichlorobenzene, cyclopentane, cyclohexane, acetic acid, formic acid or water, or in a mixture of these solvents, with use of an oxidising agent selected from the group comprising: 3-chloroperoxybenzoic acid, peroxybenzoic acid, monoperoxyphthalic acid, peroxyacetic acid, peroxyformic acid, hydrogen peroxide, sodium hypochlorite and potassium permanganate.

The third step of the process according to the invention is the exchange of the oxidised side chain in the 2-position of the pyrimidine ring for an amino group by the treatment of the compound of the formula IV with an amine of the formula V. It has proved advantageous also in this step to carry out the reaction in an inert solvent or in an inert solvent mixture. Suitable solvents for this purpose are: water, methylene chloride, chloroform, carbon tetrachloride, tetrachloroethane, trichloroethane, chlorobenzene, diethyl ether, dioxane, tetrahydrofuran, methanol, ethanol, i-propanol, diisopropyl ether, cyclohexane, dichlorobenzene, toluene, xylene, dimethylformamide, acetonitrile, dimethyl sulfoxide, acetone, 2-butanone or cyclohexanone. The reaction temperatures are generally between 20° and 100° C. Depending on the nature of the reactants of the formulae IV and V, the application of an elevated pressure of 1 bar to 100 bar, preferably of 1 bar to 20 bar, can be of advantage. The reaction vessel used in this case can be for example an autoclave.

A preferred embodiment of the third stage of the process according to the invention consists in performing the reaction of a compound of the formula IV with an amine of the formula V to give the fluoroalkoxyaminopyrimidine of the formula I at a temperature of between 20° and 100° C. under a pressure of between 1 bar and 20 bar in a solvent selected from the group comprising: water, methylene chloride, chloroform, carbon tetrachloride, trichloroethane, tetrachloroethane, chlorobenzene, diethyl ether, dioxane, tetrahydrofuran, methanol, ethanol, i-propanol, diisopropyl ether, dichlorobenzene, toluene, xylene, dimethylformamide, cyclohexane, acetonitrile, dimethyl sulfoxide, acetone, 2-butanone and cyclohexanone, or in a mixture of these solvents.

In a preferred form of the process according to the invention for producing the fluoroalkoxyaminopyrimidines of the formula I, the process comprises performing the reaction of the compound of the formula II to the compound of the formula III at a temperature of between 20° and 100° C., under a pressure of 1 bar to 20 bar, in the presence of a base selected from the group comprising: sodium hydride, calcium hydride, sodium hydroxide, potassium hydroxide, sodium carbonate and potassium carbonate, and in a solvent selected from the series: dioxane, tetrahydrofuran, methanol, ethanol, i-propanol, acetone, 2-butanone, water, dimethylformamide, acetonitrile and dimethyl sulfoxide, or in a mixture of these solvents; carrying out the oxidation of the compound of the formula III to the compound of the formula IV at a temperature of between −20° and +25° C. in a solvent selected from the group: methylene chloride, chloroform, carbon tetrachloride, tetrachloroethane, trichloroethane, chlorobenzene, dichlorobenzene, trichlorobenzene, cyclopentane, cyclohexane, acetic acid, formic acid and water, or in a mixture of these solvents, with the use of an oxidising agent selected from the group comprising: 3-chloroperoxybenzoic acid, peroxybenzoic acid, monoperoxyphthalic acid, peroxyacetic acid, peroxyformic acid, hydrogen peroxide, sodium hypochlorite and potassium permanganate; and subsequently performing the reaction of the compound of the formula IV with the amine of the formula V to obtain the fluoroalkoxyaminopyrimidine of the formula I at a temperature of between 20° and 100° C, under a pressure of between 1 bar and 20 bar, in a solvent selected from the group comprising: water, methylene chloride, chloroform, carbon tetrachloride, trichloroethane, tetrachloroethane, chlorobenzene, diethyl ether, dioxane, tetrahydrofuran, methanol, ethanol, i-propanol, diisopropyl ether, dichlorobenzene, toluene, xylene, dimethylformamide, cyclohexane, acetonitrile, dimethyl sulfoxide, acetone, 2-butanone and cyclohexanone, or in a mixture of these solvents.

It is possible if desired, in a variant of this process, to perform the reaction of the compound of the formula II to the compound of the formula III and the reaction of the compound of the formula III to the compound of the formula IV independently of one another in a liquid two-phase system in the presence of a phase-transfer catalyst. Examples of customarily employed phase transfer catalysts are, in particular, quaternary ammonium salts, ammonium hydroxides, phosphonium salts and crown ethers. Suitable ammonium salts or ammonium hydroxides are especially those of the group: benzyltrialkylammonium hydroxide or tetraalkylammonium hydroxide, benzyltrialkylammonium bisulfate or tetraalkylammonium bisulfate, and benzyltrialkylammonium halide or tetraalkylammonium halide, in which the alkyl groups advantageously contain 1 to 4 carbon atoms, for example benzyltriethylammonium chloride, tetra-n-butylammonium hydroxide and benzyltrimethylammonium chloride. A tetraalkylammonium halide is particularly suitable, especially tetra-n-butylammonium bromide. Examples of phosphonium salts are: tributylhexadecylphosphonium bromide, ethyltriphenylphosphonium bromide, tetraphenylphosphonium chloride, benzyltriphenylphosphonium iodide, triphenyl-n-propylphosphonium bromide and tetrabutylphosphonium chloride. Phase transfer catalysts that can be used are in general also the following crown ethers: 12-crown-4, 15-crown-5, 18-crown-6, dibenzo-18-crown-6, dicyclohexano-18-crown-6 and dicyclohexano-24-crown-8.

The process according to the invention is preferably used to produce compounds of the subgroup Ia

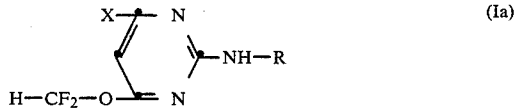

(Ia)

wherein R is hydrogen or $C_1$-$C_2$-alkyl, and X is $C_1$-$C_2$-alkyl, $C_1$-$C_2$-alkoxy or $C_1$-$C_2$-haloalkoxy. The process is however more especially suitable for producing 2-amino-4-difluoromethoxy-6-methylpyrimidine.

To be regarded as a specifically preferred embodiment is the process according to the invention which comprises reacting a thiopyrimidine of the formula II in dioxane in the presence of aqueous sodium hydroxide solution, at a temperature of between 20° and 100° C., with difluorochloromethane, difluorobromomethane, tetrafluoroethylene, perfluoropropylene, trifluorobromoethylene or trifluorochloroethylene; converting the resulting compound of the formula III, in methylene chloride with m-chloroperoxybenzoic acid, or in a glacial acetic acid/methylene chloride mixture with potassium permanganate, at a temperature of between −20° and +25° C., or in glacial acetic acid with an aqueous hydrogen peroxide solution at a temperature of between 70° and 90° C., by oxidation into a compound of the formula IV; and then treating this compound, at a temperature of between 20° and 100° C. under a pressure of between 1 bar and 20 bar in a methylene chloride/water mixture, with an amine of the formula V.

The starting compounds of the formula II are known from the literature, or they can be produced by methods analogous to known methods. The intermediates of the formula III and of the formula IV are novel, and were developed specially for performing the process according to the invention. The compounds of the formulae III and IV form therefore a part of the subject matter of the present invention. The compounds of the formula V are obtainable commercially. Data concerning the production and the properties of the compounds of the formula II are given in the following literature: Chem. Listy 52, 357 (1958).

The fluoroalkoxyaminopyrimidines of the formula I can be produced by application of the novel production process according to the invention in a manner specially adapted to meet the requirements of large-scale technology. In particular, the yield of the product of the formula I compared with that obtainable by the process known from European Patent Application No. 70804 is greatly improved. At the same time, the yield of product per unit of volume employed increases. The fluoroalkylation reaction can be performed until a complete conversion is obtained, the result of which is a considerable simplification of the processing techniques, as well as an appreciable reduction in the expenditure otherwise necessary to effect the separation and regeneration of the unreacted starting material and isolation of the reaction product from the reaction solution.

The following Examples serve to further illustrate the present invention. The Examples 2 to 4, which describe only individual reaction steps, are to be understood as being variants of the corresponding steps in a complete reaction sequence.

EXAMPLE 1

2-Amino-4-difluoromethoxy-6-methylpyrimidine (a) 2-Methylthio-4-difluoromethoxy-6-methylpyrimidine 218.7 g (1.4 mols) of 2-methylthio-4-hydroxy-6-methylpyrimidine are suspended in 1.12 litres of dioxane, and 1500 g (11.2 mols) of 30% aqueous sodium hydroxide solution are added. The suspension is heated to 80° C., and into this hot suspension are passed, in the course of 3 hours, 242 g (2.8 mols) of difluorochloromethane. The pale yellow suspension obtained is cooled to 20° C. and filtered. The residue is washed with dioxane and dried to thus yield 210 g of 2-methylthio-4-difluoromethoxy-6-methylpyrimidine. The filtrate is extracted with methylene chloride, and the organic phase is washed with water and concentrated by evaporation to obtain, as crystalline residue, a further 79 g of the desired product. The overall yield obtained in this manner is 289 g of 2-methylthio-4-difluoromethoxy-6-methylpyrimidine (100% of theory), m.p. 40-42° C.

(b) 2-Methylsulfonyl-4-difluoromethoxy-6-methylpyrimidine

A solution of 70.0 g (0.44 mol) of potassium permanganate in 700 ml of water is added dropwise to a solution of 30.9 g (0.15 mol) of 2-methylthio-4-difluoromethoxy-6-methylpyrimidine, 0.75 g of 18-crown-6-ether and 30 ml of glacial acetic acid in 1400 ml of methylene chloride. This mixture is stirred for 3 hours at a temperature of between 20° and 25° C., and sodium hydrogen sulfite solution is then added until the precipitated manganese oxide ($MnO_2$) is dissolved. The organic phase of the reaction mixture is separated, washed with water, dried over sodium sulfate and concentrated by evaporation. There are thus obtained, as a colourless residue, 33.8 g (95% of theory) of 2-methylsulfonyl-4-difluoromethoxy-6-methylpyrimidine, m.p. 86°-88° C.

(c) 4.0 g (0.017 mol) of 2-methylsulfonyl-4-difluoromethoxy-6-methylpyrimidine are suspended in 60 ml of chloroform. This suspension is saturated with gaseous ammonia, and then stirred for 3 hours at a temperature of between 20° and 25° C. The reaction mixture is subsequently diluted with 50 ml of methylene chloride; the organic phase is separated, washed with water and concentrated by evaporation. There are obtained, as crystalline residue, 2.5 g (85% of theory) of 2-amino-4-difluoromethoxy-6-methylpyrimidine, m.p. 137°-139° C.

EXAMPLE 2

2-Methylsulfonyl-4-difluoromethoxy-6-methylpyrimidine

A suspension of 101.5 g (0.5 mol) of 3-chloroperoxybenzoic acid in 300 ml of methylene chloride is cooled to a temperature of between 0° and +5° C., and there is then added dropwise a solution of 2-methylthio-4-difluoromethoxy-6-methylpyrimidine in 50 ml of methylene chloride. After the reaction mixture has been stirred for a further hour at the same temperature, 100 ml of methylene chloride are added; the mixture is subsequently washed with sodium hydrogen carbonate solution and water, dried over sodium sulfate and concentrated by evaporation. Recrystallisation of the residue from a methylene chloride/petroleum ether mixture yields 45 g (80% of theory) of 2-methylsulfonyl-4-difluoromethoxy-6-methylpyrimidine, m.p. 88°-91° C.

EXAMPLE 3

2-Methylsulfinyl-4-difluoromethoxy-6-methylpyrimidine

A suspension of 20.6 g (0.1 mol) of 3-chloroperoxybenzoic acid in 100 ml of methylene chloride is cooled to a temperature of between −15° C. and −20° C., and there is then added dropwise a solution of 20.6 g (0.1 mol) of 2-methylthio-4-difluoromethoxy-6-methylpyrimidine in 50 ml of methylene chloride. After the reaction mixture has been stirred for 1 hour at the same temperature, it is diluted with methylene chloride; it is subsequently washed with a sodium hydrogen carbonate solution and water, dried over sodium sulfate and concentrated by evaporation. Crystallisation of the residue from a methylene chloride/petroleum ether mixture yields 21.6 g (97% of theory) of 2-methylsulfinyl-4-difluoromethoxy-6-methylpyrimidine, m.p. 105°-107° C.

EXAMPLE 4

2-Methylamino-4-difluoromethoxy-6-methylpyrimidine 30 ml of a 40% aqueous methylamine solution are added, at a temperature of between 20° and 25° C., to 2.2 g (0.009 mol) of 2-methylsulfonyl-4-difluoromethoxy-6-methylpyrimidine. The mixture warms up to a temperature of 60° C. The reaction mixture is subsequently stirred for half an hour at the same temperature; it is then cooled and 50 ml of methylene chloride are added. The organic phase is separated, dried over sodium sulfate and concentrated by evaporation. Crystallisation of the residue from a methylene chloride/petroleum ether mixture yields 1.4 g (74% of theory) of 2-methylamino-4-difluoromethoxy-6-methylpyrimidine, m.p. 129.5°-131° C.

EXAMPLE 5

4,6-Bis(difluoromethoxy)-2-aminopyrimidine (a) 4,6-Bis(difluoromethoxy)-2-methylthiopyrimidine 160 g of difluorochloromethane are introduced at a temperature of between 75° and 80° C., within 15 minutes, into a mixture of 130 g of 4,6-dihydroxy-2-methylthiopyrimidine, 750 ml of a 30% aqueous sodium hydroxide solution and 1000 ml of dioxane. The precipitating organic phase is separated, and to the aqueous phase are added a further 1000 ml of dioxane; into this mixture are then passed afresh 160 g of difluorochloromethane and, after separation of the organic phase, this operation is repeated. The combined organic phases are concentrated by evaporation, and the residue is poured into ice-water. After separation and drying of the precipitate, the yield is 48.2 g (24.8% of theory) of 4,6-bis(difluoromethoxy)-2-methylthiopyrimidine, m.p. 46°-48° C.

(b) 4,6-Bis(difluoromethoxy)-2-methylsulfonylpyrimidine 6.0 ml of a 30% aqueous hydrogen peroxide solution are added dropwise, at a temperature of between 80° and 85° C., to a solution of 1.7 g of 4,6-bis(difluoromethoxy)-2-methylthiopyrimidine in 20 ml of glacial acetic acid, and stirring is maintained for 2 hours at the same temperature. The reaction mixture is subsequently taken up in water, and extracted with methylene chloride. After the organic phase has been concentrated by evaporation and the residue recrystallised from diethyl ether, the yield is 1.8 g (94% of theory) of 4,6-bis(difluoromethoxy)-2-methylsulfonylpyrimidine, m.p. 95°-96° C.

(c) To a solution of 1.0 g of 4,6-bis(difluoromethoxy)-2-methylsulfonylpyrimidine in 20 ml of methylene chloride are added, with vigorous stirring, 5 ml of a 30% aqueous ammonia solution, in the course of which the reaction mixture warms up and is stirred for a further 2 hours. The solution is subsequently concentrated by evaporation and crystallised to thus obtain, in quantitative yield, (0.8 g) 4,6-bis(difluoromethoxy)-2-aminopyrimidine, m.p. 67°-69° C.

The intermediates and final products listed in the following Tables are obtained in an analogous manner. These compounds can be produced by the process according to the invention or they occur as intermediates during the carrying out of the process.

TABLE 1

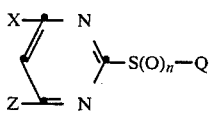

| Comp. No. | Q | n | X | Z | Physical data |
|---|---|---|---|---|---|
| 1.1 | $CH_3$ | 0 | $CH_3$ | $OCHF_2$ | m.p. 40–42° C. |
| 1.2 | $CH_3$ | 1 | $CH_3$ | $OCHF_2$ | m.p. 105–107° C. |
| 1.3 | $CH_3$ | 2 | $CH_3$ | $OCHF_2$ | m.p. 88–91° C. |
| 1.4 | $C_6H_5$ | 0 | $CH_3$ | $OCHF_2$ | b.p. 108° C./0,04 bar |
| 1.5 | $C_6H_5$ | 2 | $CH_3$ | $OCHF_2$ | m.p. 122–123° C. |
| 1.6 | $CH_3$ | 0 | $OCHF_2$ | $OCHF_2$ | m.p. 46–48° C. |
| 1.7 | $CH_3$ | 1 | $OCHF_2$ | $OCHF_2$ | m.p. 70–73° C. |
| 1.8 | $CH_3$ | 2 | $OCHF_2$ | $OCHF_2$ | m.p. 95–96° C. |
| 1.9 | $C_2H_5$ | 0 | $OCHF_2$ | $OCHF_2$ | m.p. 14–16° C. b.p. 85–90° C./0,05 bar |
| 1.10 | $C_6H_5-CH_2-$ | 0 | $OCHF_2$ | $OCHF_2$ | m.p. 40–45° C. |
| 1.11 | $C_2H_5$ | 2 | $OCHF_2$ | $OCHF_2$ | |
| 1.12 | $C_6H_5-CH_2-$ | 2 | $OCHF_2$ | $OCHF_2$ | |
| 1.13 | $CH_3$ | 0 | $CH_3$ | $OCF_2-CHF_2$ | |
| 1.14 | $CH_3$ | 2 | $CH_3$ | $OCF_2-CHF_2$ | |

TABLE 2

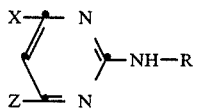

| Comp. No. | R | X | Z | Physical data |
|---|---|---|---|---|
| 2.1 | H | $CH_3$ | $OCHF_2$ | m.p. 137–139° C. |
| 2.2 | $CH_3$ | $CH_3$ | $OCHF_2$ | m.p. 129,5–131° C. |
| 2.3 | H | $OCHF_2$ | $OCHF_2$ | m.p. 67–69° C. |
| 2.4 | $C_2H_5$ | $OCHF_2$ | $OCHF_2$ | m.p. 72–74° C. |
| 2.5 | $C_2H_5O$ | $OCHF_2$ | $OCHF_2$ | m.p. 95–96° C. |
| 2.6 | $CH_3$ | $C_2H_5$ | $OCHF_2$ | |
| 2.7 | $CH_3O$ | $CH_3$ | $OCHF_2$ | |
| 2.8 | H | $OCH_3$ | $OCHF_2$ | |
| 2.9 | H | $CH_3$ | $OCF_2CHF_2$ | |
| 2.10 | $C_2H_5$ | $CH_3$ | $OCHF_2$ | |

What is claimed is:

1. A process for producing a fluoroalkoxyaminopyrimidine of the formula I

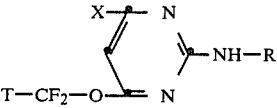

wherein R is hydrogen, $C_1-C_4$-alkyl, $C_1-C_4$-alkoxy or benzyl, X is halogen, $C_1-C_4$-alkyl, $C_1-C_4$-alkoxy, $C_1-C_4$-haloalkyl, $C_1-C_4$-haloalkoxy, $C_1-C_4$-alkylamino or di-$C_1-C_4$-alkylamino, and T is hydrogen, chlorofluoromethyl, bromofluoromethyl, difluoromethyl or 1,2,2,2-tetrafluoroethyl, characterised in that a thiopyrimidine of the formula II

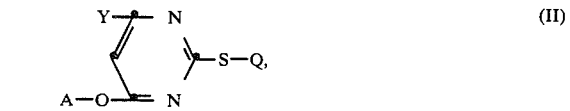

wherein Y has the meaning given for X under the formula I or is hydroxyl, Q is $C_1-C_4$-alkyl, phenyl or benzyl, and A is hydrogen, sodium, potassium or an equivalent of calcium or magnesium, is reacted with difluoromethane, difluorobromomethane, tetrafluoroethylene, perfluoropropylene, trifluorobromoethylene or trifluorochloroethylene in the presence of an inorganic base; the resulting compound compound of the formula III

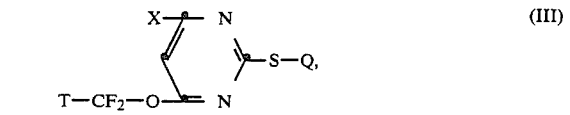

wherein T and X have the meanings defined under the formula I and Q the meanings defined under the formula II, is converted by oxidation into a compound of the formula IV

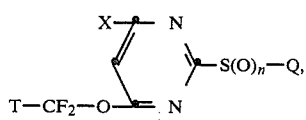

wherein T and X have the meanings defined under the formula I and Q the meanings defined under the formula II, and n is the number one or two; and this compound is treated with an amine of the formula V $$H-NH-R \qquad (V)$$

wherein R has the meaning given under the formula I.

2. A process according to claim 1, characterised in that the individual reaction steps are performed in the presence of inert solvents or inert solvent mixtures.

3. A process according to claim 1, characterised in that the reaction of the compound of the formula II to the compound of the formula III is performed in the presence of a solvent selected from the group consisting of: ethers, alcohols, ketones, water, dimethylformamide, acetonitrile and dimethyl sulfoxide, or a mixture thereof.

4. A process according to claim 3, characterised in that the solvent used is: dioxane, tetrahydrofuran, methanol, ethanol, i-propanol, acetone, 2-butanone, water, dimethylformamide, acetonitrile or dimethyl sulfoxide.

5. A process according to claim 1, characterised in that the reaction of the compound of the formula II to the compound of the formula III is performed in the presence of a base selected from the group comprising: sodium hydride, calcium hydride, sodium hydroxide, potassium hydroxide, sodium carbonate and potassium carbonate.

6. A process according to claim 1, characterised in that the reaction of the compound of the formula II to the compound of the formula III is performed under a pressure of 1 bar to 100 bar.

7. A process according to claim 1, characterised in that the reaction of the compound of the formula II to the compound of the formula III is performed under a pressure of 1 bar to 20 bar.

8. A process according to claim 1, characterised in that the reaction of the compound of the formula II to the compound of the formula III is performed in a liquid two-phase system in the presence of a phase-transfer catalyst.

9. A process according to claim 1, characterised in that the reaction of the compound of the formula II to the compound of the formula III is performed at a temperature of between 0° and 120° C.

10. A process according to claim 9, characterised in that the temperature is between 20° and 100° C.

11. A process according to claim 1, characterised in that the reaction of the compound of the formula II to the compound of the formula III is performed at a temperature of between 20° and 100° C., under a pressure of 1 bar to 20 bar, in the presence of a base selected from the group: sodium hydride, calcium hydride, sodium hydroxide, potassium hydroxide, sodium carbonate and potassium carbonate, and in a solvent selected from the group consisting of dioxane, tetrahydrofuran methanol, ethanol, i-propanol, acetone, 2-butanone, water, dimethylformamide, acetonitrile and dimethyl sulfoxide, or in a mixture of these solvents.

12. A process according to claim 1, characterised in that there is used for the conversion of the compound of the formula III into a compound of the formula IV an oxidising agent selected from the group: organic peroxides, organic peroxy acids, hypochlorites, hydrogen peroxide, potassium permanganate, osmium tetroxide and ruthenium tetroxide.

13. A process according to claim 12, characterised in that the oxidising agent used is: 3-chloroperoxybenzoic acid, peroxybenzoic acid, monoperoxyphthalic acid, peroxyacetic acid, peroxyformic acid, hydrogen peroxide, sodium hypochlorite or potassium permanganate.

14. A process according to claim 1, characterised in that the conversion of the compound of the formula III into a compound of the formula IV is performed in an inert solvent, or in an inert solvent mixture.

15. A process according to claim 14, characterised in that there is used a solvent selected from the group consisting of methylene chloride, chloroform, carbon tetrachloride, tetrachloroethane, trichloroethane, chlorobenzene, dichlorobenzene, trichlorobenzene, cyclopentane, cyclohexane, acetic acid, formic acid and water.

16. A process according to claim 1, characterised in that the reaction of the compound of the formula III to a compound of the formula IV is performed at a temperature of between −20° and +90° C.

17. A process according to claim 1, characterised in that the reaction of the compound of the formula III to a compound of the formula IV is performed at a temperature of between −20 C. and +25 C.

18. A process according to claim 1, characterised in that the oxidation of a compound of the formula III to a compound of the formula IV is performed in a liquid two-phase system in the presence of a phase transfer catalyst.

19. A process according to claim 1, characterised in that the oxidation of a compound of the formula III to a compound of the formula IV is performed at a temperature of between −20° and +25° C. in a solvent selected from the group comprising: methylene chloride, chloroform, carbon tetrachloride, tetrachloroethane, trichloroethane, chlorobenzene, dichlorobenzene, trichlorobenzene, cyclopentane, cyclohexane, acetic acid, formic acid and water, or in a mixture of these solvents, with the use of an oxidising agent selected from the group consisting of 3-chloroperoxybenzoic acid, peroxybenzoic acid, monoperoxyphthalic acid, peroxyacetic acid, peroxyformic acid, hydrogen peroxide, sodium hypochlorite and potassium permanganate.

20. A process according to claim 1, characterised in that the reaction of a compound of the formula IV with an amine of the formula V to give the fluoroalkoxyaminopyrimidine of the formula I is performed in an inert solvent, or in an inert solvent mixture.

21. A process according to claim 1, characterised in that the reaction of a compound of the formula IV with an amine of the formula V is performed at a temperature of between 20° and 100° C.

22. A process according to claim 1, characterised in that the reaction of a compound of the formula IV with an amine of the formula V is performed under a pressure of between 1 bar and 100 bar, preferably between 1 bar and 20 bar.

23. A process according to claim 20, characterised in that the solvent is selected from the group consisting of water, methylene chloride, chloroform, carbon tetrachloride, tetrachloroethane, trichloroethane, chlorobenzene, diethyl ether, dioxane, tetrahydrofuran, methanol, ethanol, i-propanol, diisopropyl ether, cyclohexane, dichlorobenzene, toluene, xylene, dimethylformamide, acetonitrile, dimethyl sulfoxide, acetone, 2-butanone and cyclohexanone.

24. A process according to claim 1, characterised in that the reaction of a compound of the formula IV with an amine of the formula V to give the fluoroalkoxyaminopyrimidine of the formula I is performed at a temperature of between 20° and 100° C., under a pressure of between 1 bar and 20 bar, in a solvent selected from the group consisting of: water, methylene chloride, chloroform, carbon tetrachloride, trichloroethane, tetrachloroethane, chlorobenzene, diethyl ether, dioxane, tetrahydrofuran, methanol, ethanol, i-propanol i-propanol, diisopropyl ether, dichlorobenzene, toluene, xylene, dimethylformamide, cyclohexane, acetonitrile, dimethyl sulfoxide, acetone, 2-butanone and cyclohexanone, or in a mixture of these solvents.

25. A process according to claim 1, characterised in that the reaction of the compound of the formula II to the compound of the formula III is performed at a temperature of between 20° and 100° C., under a pressure of 1 bar to 20 bar, in the presence of a base selected from the group consisting of sodium hydride, calcium hydride, sodium hydroxide, potassium hydroxide, sodium carbonate and potassium carbonate, and in a solvent selected from the group consisting of dioxane, tetrahydrofuran, methanol, ethanol, i-propanol, acetone, 2-butanone, water, dimethylformamide, acetonitrile and dimethyl sulfoxide, or in a mixture of these solvents; and that the oxidation of the compound of the formula III to the compound of the formula IV is performed at a temperature of between −20° and −25° C. in a solvent selected from the group consisting of: methylene chloride, chloroform, carbon tetrachloride, tetrachloroethane, trichloroethane, chlorobenzene, dichlorobenzene, trichlorobenzene, cyclopentane, cyclohexane, acetic acid, formic acid and water, or in a mixture of these solvents, with the use of an oxidising agent selected from the group consisting of 3-chloroperoxybenzoic acid, peroxybenzoic acid, monoperoxyphthalic acid, peroxyacetic acid, peroxyformic acid, hydrogen peroxide, sodium hypochlorite and potassium permanganate; and that the reaction of the compound of the formula IV with the amine of the formula V to give the fluoroalkoxyaminopyridine of the formula I is performed at a temperature of between 20° and 100° C., under a pressure of between 1 bar and 20 bar, in a solvent selected from the group consisting of water, methylene chloride, chloroform, carbon tetrachloride, trichloroethane, tetrachloroethane, chlorobenzene, diethyl ether, dioxane, tetrahydrofuran, methanol, ethanol, i-propanol, diisopropyl ether, dichlorobenzene, toluene, xylene, dimethylformamide, cyclohexane, acetonitrile, dimethyl sulfoxide, acetone, 2-butanone and cyclohexanone, or in a mixture of these solvents.

26. A process according to claim 25, characterised in that the reaction of the compound of the formula II to the compound of the formula III and the reaction of the compound of the formula III to the compound of the formula IV are performed independently of one another in a liquid two-phase system in the presence of a phase-transfer catalyst.

27. A process according to claim 1, characterised in that there is produced a compound of the formula Ia

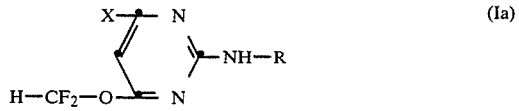

(Ia)

wherein R is hydrogen or $C_1$–$C_2$-alkyl, and X is $C_1$–$C_2$-alkyl, $C_1$–$C_2$-alkoxy or $C_1$–$C_2$-haloalkoxy.

28. A process according to claim 1, characterised in that 2-amino-4-difluoromethoxy-6-methylpyrimidine is produced.

29. A process for producing a compound of the formula I, characterised in that a thiopyrimidine of the formula II is reacted in dioxane in the presence of an aqueous sodium hydroxide solution, at a temperature of between 20° and 100° C., with difluorochloromethane, difluorobromomethane, tetrafluoroethylene, perfluoropropylene, trifluorobromoethylene or trifluorochloroethylene, the resulting compound of the formula III is converted in methylene chloride with m-chloroperoxybenzoic acid, or in a glacial acetic acid/methylene chloride mixture with potassium permanganate, at a temperature of between −20° and +25° C., or in glacial acetic acid with aqueous hydrogen peroxide solution at a temperature of between 70° and 90° C., by oxidation into a compound of the formula IV, and this compound is treated at a temperature of between 20° and 100° C., under a pressure of between 1 bar and 20 bar, in a methylene chloride/water mixture with an amine of the formula V.

30. A compound of the formula III

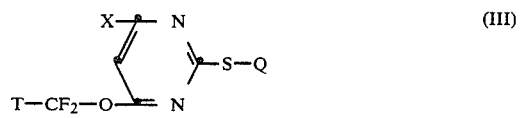

(III)

wherein T and X have the meanings defined under the formula I in claim 1, and Q is $C_1$–$C_4$-alkyl, phenyl or benzyl.

31. A compound of the formula IV

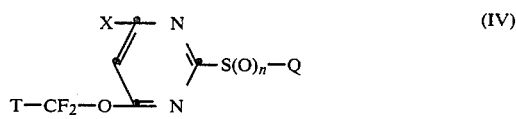

(IV)

wherein T and X have the meanings defined under the formula I in claim 1, and Q is $C_1$–$C_4$-alkyl, phenyl or benzyl, and n is the number one or two.

* * * * *